United States Patent [19]

MacAnally

[11] 4,148,551

[45] Apr. 10, 1979

[54] MODULAR ROD LENS ASSEMBLY AND METHOD OF MAKING THE SAME

[75] Inventor: Richard B. MacAnally, Altadena, Calif.

[73] Assignee: American Hospital Supply Corporation, Evanston, Ill.

[21] Appl. No.: 795,405

[22] Filed: May 9, 1977

[51] Int. Cl.² .............................................. G02B 23/16
[52] U.S. Cl. ...................................... 350/54; 350/70; 350/178; 350/242; 350/320
[58] Field of Search ....................... 350/54, 69, 70, 80, 350/128, 242, 252, 320

[56] References Cited

U.S. PATENT DOCUMENTS

| | | | |
|---|---|---|---|
| 2,453,862 | 11/1948 | Salisbury | 350/70 X |
| 3,133,143 | 5/1964 | Strang et al. | 350/54 X |
| 4,036,218 | 7/1977 | Yamashita et al. | 350/252 X |

Primary Examiner—John K. Corbin
Assistant Examiner—Matthew W. Koren
Attorney, Agent, or Firm—Tilton, Fallon, Lungmus & Chestnut

[57] ABSTRACT

A rod lens assembly having a flexible outer tube and a plurality of lens modules disposed in end-to-end relation therein. Each module comprises a rod lens secured within a protective cylindrical sleeve which extends axially beyond the end faces of the lens and which is provided near its ends with a pair of outwardly-projecting annular ribs. The ribs engage the inner surface of the flexible tube to support the modules in axial alignment with each other and to permit limited flexure of the outer tube without the transmission of bending or flexing forces to the modules themselves. The axial-projecting end portions of the sleeves serve as integral spacers which provide precise spacing between the opposing end faces of successive lenses when the tube is in its normal unflexed condition and which provide pivot points for the articulation of adjacent modules when the outer tube is flexed.

25 Claims, 8 Drawing Figures

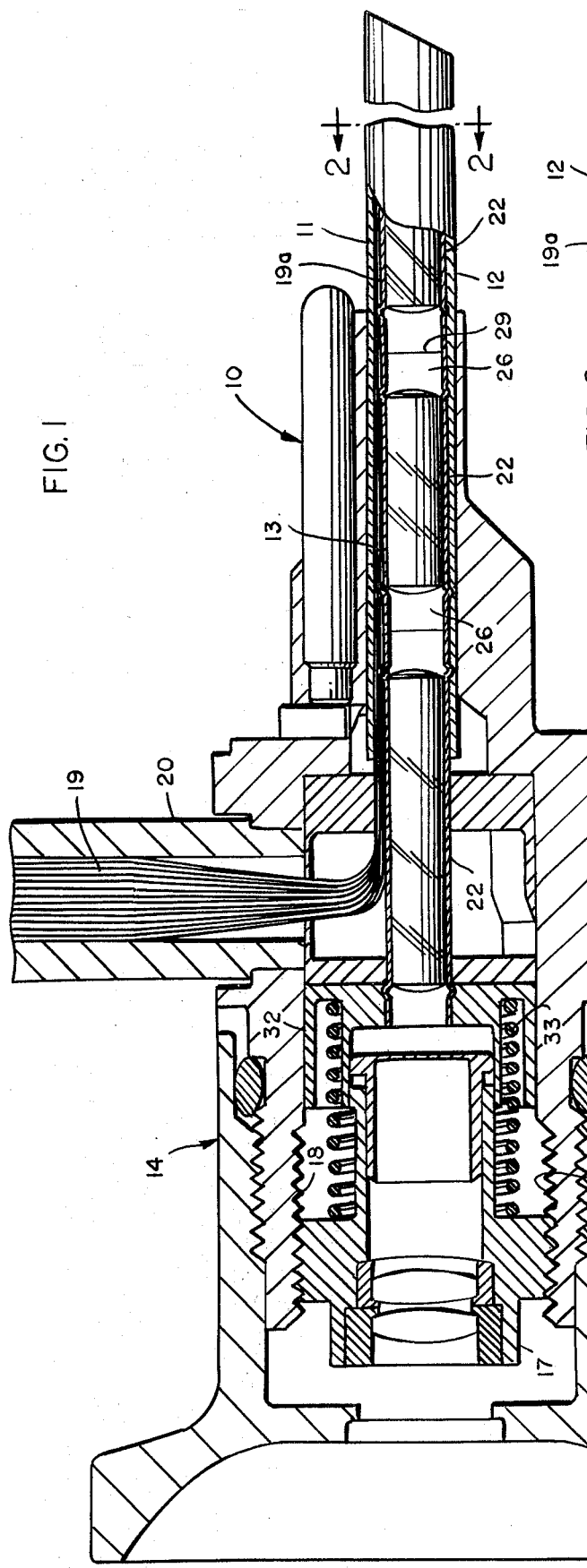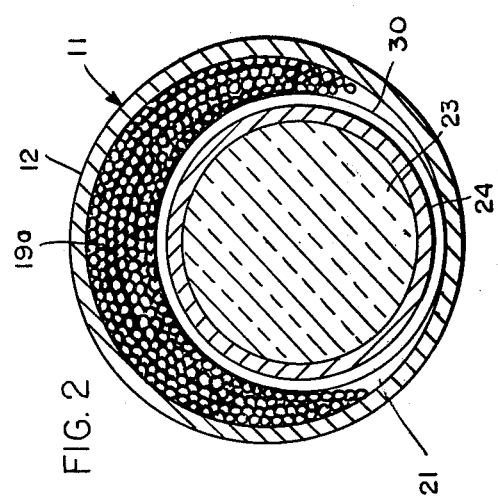

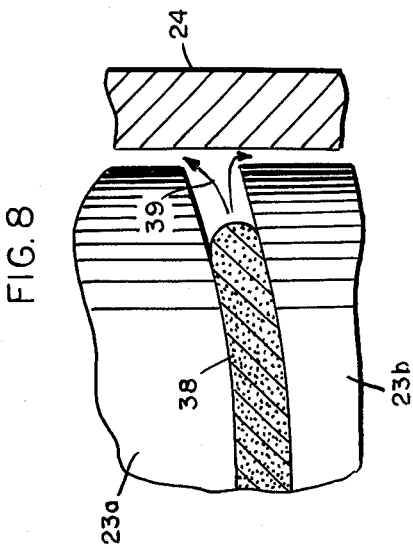
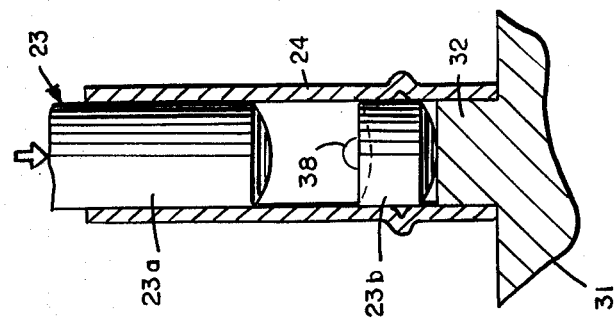
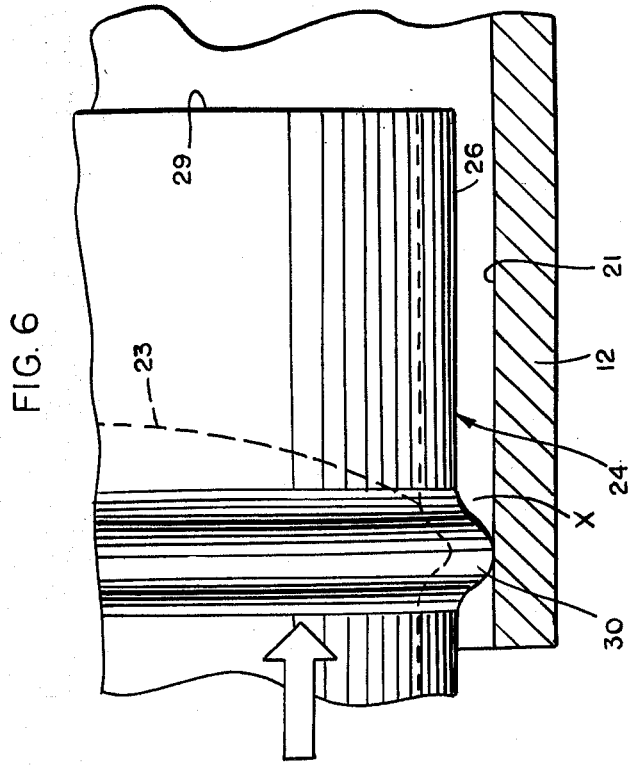

MODULAR ROD LENS ASSEMBLY AND METHOD OF MAKING THE SAME

BACKGROUND

A conventional rod lens assembly comprises a small-bore flexible tube containing a series of cylindrical rod lenses maintained in axially-spaced relation by small discrete cylindrical sleeves or spacers positioned between the lenses, as illustrated, for example, in U.S. Pat. No. 3,257,902. Even where the wall thickness of the spacers is kept to a minimum and care is taken to insure that the annular ends of those spacers contact the lenses only at their outer edges, such spacers nevertheless significantly reduce the light and image transmitting properties of the lenses by rendering portions of their end faces optically inoperative. In addition, flexure of such an assembly in use may cause the spacing sleeves to abrade or damage the edges and end faces of the lenses, not only resulting in the creation of objectionable debris but also causing possible changes in the critical distances between adjacent lenses.

An even more serious problem inherent in the construction of a typical rod lens system as so described is the possibility that flexure of the assembly may result in transverse fracture of one or more of the glass lenses, thereby rendering the entire system inoperative and requiring either costly and time-consuming repair or total replacement of the entire assembly. The seriousness of the problem is compounded by the fact that an endoscope containing such a rod lens system is commonly used in conjunction with working elements, deflecting bridges, grasping forceps, lithotrites, and other relatively heavy surgical or urological instruments which, if brought into forceful accidental engagement with the lens-containing tube of such an endoscope, might easily cause flexure of the tube and fracture one or more of the lenses.

The use of spacers to set the spacing between successive rod lenses of a series during assembly thereof has the further disadvantage that even a slight variation from the optimum length of seach sleeve could result in a tolerance buildup which might substantially impair the optical properties of the final product. Conversely, the almost-microscopic adjustments in the axial positioning of the lenses which might be needed to provide the best optical performance for the lens train as a whole would be extremely difficult if not virtually impossible to achieve in a system where sleeves must be inserted to set the spacing between successive lenses of the series.

SUMMARY

This invention is concerned with a modular rod lens assembly, an its method of construction, which overcome the aforementioned disadvantages and other shortcomings of the prior art. The modular assembly has exceptional durability, is capable of withstanding substantial flexure of the outer tube without fracturing or damaging the glass lenses contained therein, achieves an extremely high level of precision in the spacing of the end faces of successive lenses, insures that such critical spacing will be maintained despite repeated flexure of the outer tube, and eliminates the need for, and undesirable effects of, the discrete spacer elements of the prior art. The invention also facilitates the manufacture of an optically superior product by permitting thorough cleaning and/or optical testing of the lenses after the modules have been fabricated and prior to final assembly. Even in the final stage of assembly, when the lens modules are urged into proper positions within the outer tube or barrel, the contact between such modules and the bore of the tube virtually eliminates any possibility that microscopic particulate matter might become entrapped between the opposing end faces of successive rod lenses.

Briefly, the modular rod lens assembly comprises an outer tube or barrel and a plurality of lens modules disposed in end-to-end relation therein. Each module comprises a rod lens (which may be a grouping of rod lens elements) terminating at its ends in a pair of oppositely-directed end faces, and a protective sleeve structure extending about the rod lens and providing a pair of tubular end portions which project endwise beyond the end faces of the lens. Annular ribs projecting radially outwardly adjacent the ends of each module provide bearing surfaces which engage the inside of the outer tube to maintain the lens modules in axial alignment. Such ribs also perform the important additional function of defining annular spaces about the modules to accommodate displaced wall portions of the outer tube when that tube is bent or flexed, thereby preventing the bending forces from being transmitted directly to each glass rod lens. As the outer tube flexes, a pivotal action occurs between the tubular end portions of the sleeves of successive modules of the series, such pivotal action resulting in an articulation of the modules which protects against the transmission of damaging forces to the fragile glass lenses.

In a preferred embodiment of the invention, the sleeve structure of each module takes the form of a rigid generally-cylindrical casing having integral intermediate and end portions. The rod lens is secured within the intermediate portion and a pair of annular ribs, interposed between the intermediate and end portions, project radially outwardly from the casing to provide bearing surfaces for limited contact with the inside wall surface of the outer tube or barrel. The annular ribs are preferably formed integrally with the tubular casing.

In an endoscope in which such a rod lens assembly is adapted for use, spring means are provided for maintaining the lens modules in an end-to-end contact whether the outer tube is flexed or straight. The annular ribs of the modules are slidably engagable with the inside surface of the tube to permit limited axial adjustment of the modules relative to the tube as such modules pivot with respect to each other during bending and unbending of the tube.

The modular construction, with spacers effectively provided as integral portions of each module, gives rise to improved methods of construction which constitute further aspects of this invention. After precisely locating and securing a rod lens (including a group of lenses or lens elements) in its rigid protective sleeve, the module may be thoroughly cleansed to remove all particulate matter from the exposed surfaces, and particularly from the end faces of the lens, and may then be optically tested in combination with other modules which will form a relay system in the final assembly. The group of modules which constitute the relay systen may if desired be preassembled, as by wrapping the abutting ends of the modules in a suitable shrinkable plastic film which will not interfere with the pivotal action between adjacent modules in the final assembly. After thorough cleaning of the modules, and whatever testing and preassembling steps are desired, the modules are inserted endwise into the outer tube or barrel. During such insertion and movement of the modules into their final positions, only the ribs of the modules are brought into contact with the inside surface of the barrel. Since the ribs are spaced from the ends of the sleeves, and since the ends of the sleeves do not directly contact the inside surface of the barrel during such an assembly step, the possibility that particulate matter might be scraped or otherwise directed into the space between opposing end faces of adjacent lenses of the final assembly is eliminated or at least greatly reduced.

Other objects and advantages of the invention will become apparent from the specification and drawings.

DRAWINGS

FIG. 1 is an enlarged sectional view of a portion of an endoscope equipped with a modular rod lens assembly embodying the present invention.

FIG. 2 is a greatly enlarged cross sectional view of the rod lens assembly embodying the invention.

FIG. 3 is a longitudinal sectional view of a lens module.

FIG. 6 is a greatly enlarged fragmentary longitudinal sectional view illustrating a lens module as it is being axially advanced into position within an outer tube.

FIG. 7 illustrates a modification of the module assembly procedure of FIG. 5.

FIG. 8 is an enlarged fragmentary view illustrating a further step in the modified procedure of FIG. 7.

DETAILED DESCRIPTION OF PREFERRED EMBODIMENTS

Figure 4:
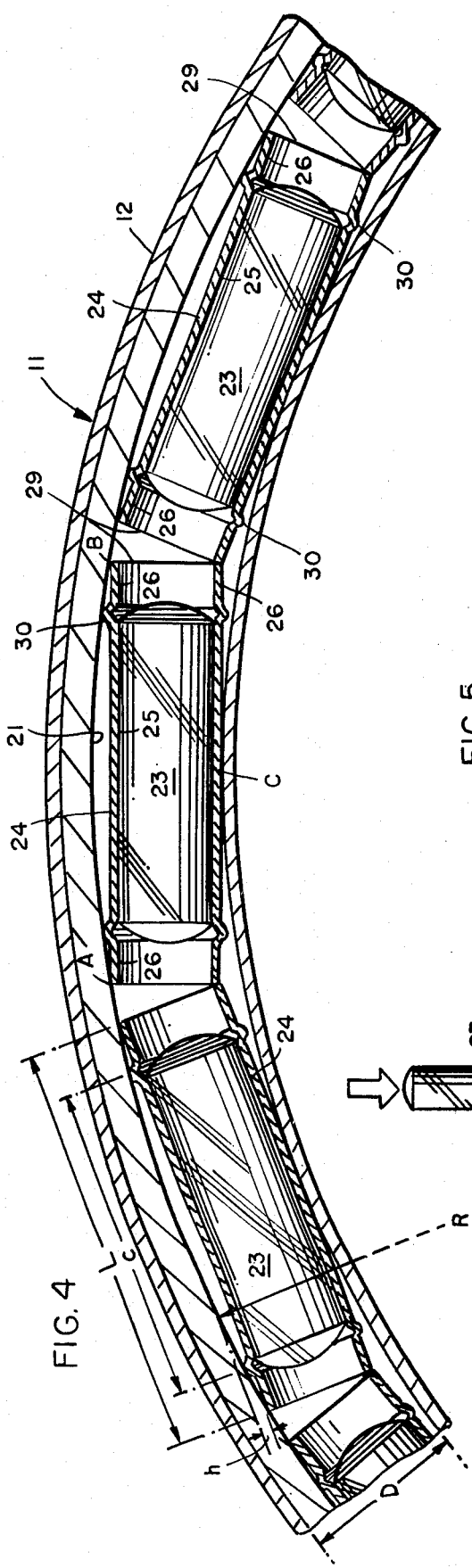
FIG. 4 is a somewhat schematic longitudinal sectional view illustrating the relationship of parts when the outer tube of a rod lens assembly embodying this invention is flexed.

Referring to the drawings, FIG. 1 illustrates an endoscope 10 equipped with a modular rod lens assembly 11 embodying the present invention. The lens assembly comprises an outer tube or barrel 12 formed of a flexible and semirigid (i.e., non-brittle) material such as stainless steel. The proximal end of the normally-straight tube 12 is secured within the bore 13 of an eyepiece assembly designated generally by the numeral 14. The eyepiece assembly includes a housing 15, an eyepiece 16 threadedly connected to the housing, and an eyepiece lens fitting 17 threadedly secured within an enlarged bore 18 of the housing.

Illumination for the field view is provided by a light-transmitting glass fiber bundle 19 which is operatively connected to a suitable light source (not shown) and which enters the eyepiece assembly through coupling 20. Although a light-transmitting fiber bundle is important for endoscope operation, the bundle 19 is conventional as shown and is not essential for purposes of the present invention. For that reason, in describing the rod lens assembly 11, that portion 19a of the fiber bundle which extends through the tube 12 will be regarded simply as a part of that outer tube or barrel. Thus, the outer tube 12, including the fiber bundle 19a which lines that tube, defines a longitudinal bore 21 which supports a plurality of rod lens modules 22 in end-to-end relation. In FIG. 2, the fiber bundle lining tube 12 is crescent-shaped in cross section with the result that bore 21 is offset from the longitudinal axis of the tube; however, if desired the fibers may be distributed uniformly to form an annular lining that defines a bore coaxial with the tube.

Each module 22 comprises a cylindrical rod lens 23 secured within a protective tubular sleeve or jacket 24. A typical module is depicted in FIG. 3. The rod lens shown in that figure happens to be composed of lens elements 23a and 23b cemented together to form a composite rod lens of a general type well known in the art. It is to be understood that the use of multiple lens elements in fabricating a single rod lens is intended primarily to correct for spherical and/or chromatic aberrations and that in appropriate cases the rod lens may be formed integrally from a single piece of glass. Conversely, there may be instances where a rod lens consists of segments which are spaced axially apart within a single sleeve or jacket 24. The term "rod lens" as used herein is intended to encompass all such variations.

In the embodiment illustrated, the sleeve 24 of each module includes an elongated intermediate portion 25 and a pair of end portions 26. The rod lens 23 is secured within the intermediate portion 25 with the tubular end portions 26 extending axially beyond the oppositely-directed end faces 27 and 28 of the lens. Each end portion terminates in an annular contact surface 29 which extends along a plane normal to the longitudinal axis of the sleeve. As shown in FIG. 1, when the instrument is in its normal operating condition the contact surfaces 29 of successive modules abut each other and the tubular end portions which so engage each other serve to space the opposing end faces of the rod lenses of such modules a precise and predetermined distance apart.

The protective sleeves or jackets 24 may be formed of steel or any other material having sufficient rigidity, strength, and dimensional stability to serve a protective function and to insure precise spacing between the ends of successive rod lenses. In addition, the material of the sleeves must be non-abrading and non-fragmenting; that is, the articulation which occurs as the ends of adjacent sleeves pivotally engage each other (FIG. 4) must not result in the generation of particles that could become entrapped between the optical end surfaces of successive lenses.

Near the ends of each lens module 22 is an annular and outwardly (radially) projecting rib 30, as shown clearly in FIGS. 3 and 4. In the preferred embodiment illustrated, each rib is disposed between the intermediate portion 25 and an end portion 26 of the tubular sleeve 25 and is formed integrally with that sleeve. The outside diameter of each rib is the same as, or just slightly less than, the inside diameter of bore 21 and, in any case, is substantially greater than the outside diameter of the remainder of the sleeve or jacket 24. As a result, the pair of spaced ribs near the ends of each sleeve provide narrow bearing surfaces for engaging the inside surface of the outer tube and for supporting the lens modules therein.

FIG. 4 depicts in somewhat schematic fashion the relationship of parts when the outer tube 12 is flexed to a maximum extent—that is, to the greatest extent possible before bending forces are transmitted to each of the lens modules. As the normally-straight outer tube or barrel is flexed, the lens modules articulate as shown, a pivoting action occurring at some point along the contacting annular surfaces 29 of successive modules. As such articulation occurs, ribs 30 serve as bearing means for engaging the bore of the outer tube and for converting the bending forces exerted upon the outer tube into the forces which cause the modules to pivot out of longitudinal alignment. Until such time as the bending of the outer tube reaches the maximum flexure shown, only the narrow ribs 30 bear against the inside surface of the tube. When maximum flexure is reached, additional contact is made at three points A, B, and C. Points A and B are located at opposite ends of each sleeve, such points being in longitudinal alignment with each other. Point C is diametrically disposed from points A and B and is at the longitudinal midpoint of the sleeve. It is believed apparent that if the outer tube is subjected to further bending, the bending forces will be transmitted to each lens module at points A, B, and C.

The parts should be dimensioned and fabricated so that the flexure depicted in FIG. 4 far exceeds the flexure that would be encountered in normal handling and use of the assembly. Ideally, the composition of the parts is such that should be extent of flexure illustrated in FIG. 4 take place, the outer tube or barrel will have exceeded its limit of inelastic bending and will not return to its normally-straight condition when the bending forces are removed. The permanently-bent configuration of the outer tube will then serve as an indication that the instrument has been abused and that its optical performance may have been destroyed or seriously impaired.

It may be noted that when the outer tube is flexed, the pivotal action occurring at the ends of the lens modules causes slight axial displacement of the proximally-disposed modules of the series. Such axial displacement is accommodated by means of a spring-loaded support member 32 which is slidably disposed within the bore of the eyepiece and which receives the end portion of the first (i.e., most proximal) module 22 of the series. As the tube or barrel flexes, the slidable member 32 slides slightly to accommodate the longitudinal displacement of the modules which such flexure (and accompanying pivotal action of the modules) causes; when the tube returns to its normally-straight condition, spring 33 returns the modules into their original positions wherein the modules are in longitudinal alignment and their opposing end surfaces 29 are in tight circumferential engagement.

Figure 5:
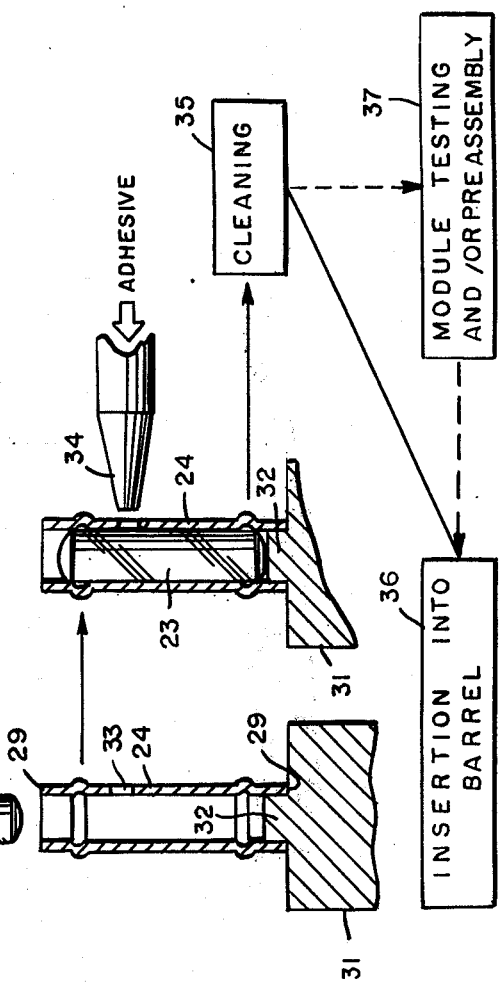
FIG. 5 is a partially diagrammatic view illustrating a sequence of fabrication steps.

The construction shown and described gives rise to improved assembly procedures which eliminate or greatly reduce any possibility that particulate matter may become entrapped between the opposing end faces of successive rod lenses or that the assembled parts might provide inferior optical performance. FIG. 5 diagramatically illustrates that precise positioning of a rod lens 23 within its sleeve 24 is readily accomplished by temporarily positioning the sleeve upon a jig 31 having a stem 32 dimensioned to be received in one end of the sleeve. The axial dimension of the stem is established so that the rod lens when fully inserted will be accurately located within the sleeve, the end faces of the lens being precise and predetermined distances from opposite end surfaces 29 of the sleeve. Thereafter, the lens is secured in place within the sleeve by any suitable means. In the illustration given, a small side opening 33 is provided in the wall of the sleeve to receive the nozzle 34 of an adhesive injector.

The completed module is than subjected to a cleaning step 35 to remove all foreign matter from the exposed surfaces and, in particular, from the optical end faces of the glass lens. The modules may be cleaned by standard ultrasonic cleaning techniques or by any other suitable washing, rinsing, and drying procedures. It is to be noted that such cleaning is particularly important in rod lens systems because, unlike camera systems, the faces of the lenses often lie in or near the image planes. Any particulate matter remaining upon the end face of a rod lens might therefore appear in the field of view when the completed assembly is put to use.

Following thorough cleaning, the rod lens modules are simply inserted into their proper positions within the bore 21 of the outer tube or barrel, such assembly step being represented diagramatically in FIG. 5 by numeral 36. As an optional additional procedure, before the final assembly stage 36, the lens modules to be used in a given instrument may be supported in end-to-end relation in the channel of a suitable jig (not shown) and optically tested. Such testing may be performed on individual rod lenses, or, more likely, on groups of such lenses which form relay systems. It is also believed apparent that all of the lens modules to be used in a single instrument may be tested simultaneously. Following test procedures 37, the optically acceptable rod lens modules may be secured in preassembled relation by bands or heat-shrinkable film (not shown) or other suitable material wrapped about the adjacent end portions of successive modules, and the entire lens train, or the groups of modules which form a relay system, may be sealed in suitable containers or wrappers for storage and future use.

To provide maximum protection for each rod lens 23, it is important that each rod lens be encased within a single integral sleeve or jacket 24. In some instances, however, it may be desirable to divide such a sleeve at a midpoint, thereby providing two sleeve sections which may or may not leave some part of the intermediate portion of a rod lens uncovered or exposed. Although such a sleeve construction would provide less protection against lens fracture, it would be otherwise identical in function to the sleeve structure already described.

In the final assembly stage 36, when the lens modules 22 are being inserted into bore 21 of the outer tube, ribs 30 slide along the surface of the bore as indicated in FIG. 6. It will be observed that the edges of the sleever 24 at the end of the module are spaced from the surface of bore 21 and, therefore, there is no scraping action that might possibly cause particulate matter to enter the open end of the sleeve where it might affect the optical performance of rod lens 23. Furthermore, since the rib 30 is spaced a substantial distance from the end surface 29 of the sleeve, any foreign matter that might possibly be scraped and/or advanced by a plowing or wiping action of the rib upon the surface of bore 21 would collect at point X well away from the open end of the sleeve. For the same reason, relative movement between rib 30 and the surface of the bore during flexure of the completely assembled instrument is not likely to generate particles that might enter the space between the opposing end faces of successive lenses.

FIGS. 7 and 8 depict a modification of the assembly procedure of FIG. 5 that may be used in those cases where a rod lens 23 is composed of more than one element. Using the same type of jig 31 previously described, a sleever 24 is fitted upon stem 32 and the first element 23b is positioned against the stem (FIG. 7). The next element 23a of the rod lens is then shifted into position. Prior to insertion of the second element, however, either that element, or the element already disposed within the sleeve, has a small quantity of liquid adhesive or cement 38 applied to its opposing face. Then, as the two elements are urged together, the liquid adhesive is forced outwardly to perform the simultaneous functions of bonding the elements together and adhesively securing the composite lens within sleever 24. Attachment to the sleeve is achieved because some of the adhesive 38 is forced laterally outwardly as indicated by arrows 39 (FIG. 8) to occupy the space between the cylindrical surface of the composite rod lens and the inside surface of sleever 24.

In all of the embodiments described, the final modules include narrow annular ribs 30 which constitute the bearing means for supporting those modules within a flexible barrel. It is to be noted that the ribs are of minimum axial dimension so that the bearing surface of each rib is preferably nothing more than an annular line and, when the parts are assembled, that narrow bearing surface actually makes only point contact with the inner surface of the barrel.

The distance between the paired ribs of each module may be varied somewhat to suit the needs and requirements of any given assembly. As previously indicated, however, an important advantage of the invention is that such ribs may be optimally positioned to allow the maximum possible barrel deflection without breaking the fragile rod lenses. Referring to FIG. 4, for a sleeve of length L, concentrically located within a barrel of inside diameter D and separated from the barrel by an annular spacing of approximately h, the minimum bending radius R of the barrel would be approximately:

$$R = h + \frac{L^2}{16h}$$

Corresponding to this condition is an optimum separation c of the supporting ribs (such separation being symmetrical relative to the longitudinal mid point of the sleeve) of approximately:

$$c = 2\sqrt{h^2 + \frac{L^2}{8} - 2hD}$$

For almost any practical embodiment of an endoscope, this last relation reduces to, and may be approximately stated as:

$$c = \frac{L}{\sqrt{2}}$$

Thus, in a typical case, where the length (L) of the sleeve is 0.73 of an inch, the inside diameter (D) of the barrel is 0.125 of an inch, and the height (h) of the ribs (i.e., the annular spacing) is 0.004 of an inch, the optimum distance (c) between such ribs should be approximately 0.512 of an inch. As indicated, such ribs should be symmetrical about a longitudinal mid point of the sleeve; that it, the ribs should be spaced equally from the longitudinal mid point of the sleeve or, conversely, should be spaced equally from the ends of the sleeve. Under such circumstances, the barrel should be capable of being bent or deflected at a uniform radius of approximately 8.33 inches before the sleever makes its three-point contact at points A, B, and C, and the deflecting forces are thereby transmitted to the module sleeves.

While in the foregoing, embodiments of the invention have been disclosed in considerable detail for purposes of illustration, it will be understood by those skilled in the art that many of these details may be varied without departing from the spirit and scope of the invention.

I claim:

1. A module for a flexible rod lens assembly, said module comprising an elongated cylindrical glass rod lens having optical end faces and being secured in a protective sleeve, said sleeve including an intermediate portion in which said elongated rod lens is secured and end portions projecting axially beyond said end faces, whereby, when a plurality of said modules are disposed in longitudinal alignment with the end portions thereof in abutting relation, said end portions of said sleeves provide spacing means for precisely spacing the optical end faces of successive elements, said sleeve also including annular bearing means projecting outwardly therefrom for supporting said module within a flexible barrel.

2. The module of claim 1 in which said bearing means comprises a pair of narrow annular ribs interposed between said intermediate and end portions, said ribs being of substantially greater outside diameter than said intermediate and end portions.

3. The module of claim 2 in which said pair of ribs are spaced uniformly from the longitudinal mid point of said module and are spaced apart a distance of approximately $$c = \frac{L}{\sqrt{2}}$$

where c is the distance between the ribs and L is the total length of the sleeve.

4. The module of claim 1 in which each of said end portions terminates in an end surface extending along a plane normal to the axis of said rod lens.

5. The module of claim 1 in which said cylindrical rod lens comprises a plurality of lens elements disposed in axial alignment.

6. The module of claim 5 in which said lens elements are adhesively secured together.

7. A modular rod lens assembly comprising a straight semi-rigid tube capable of limited flexure, and a series of lens modules disposed in end-to-end relation therein, each module comprising an elongated rod lens having a pair of oppositely-directed end faces, and sleeve means having an intermediate portion containing said elongated rod lens and a pair of tubular end portions projecting endwise beyond said end faces, said sleeve means of each module being permanently secured to said rod lens and including narrow annular ribs projecting radially outwardly adjacent opposite ends of each module, said ribs being in bearing engagement with the inside surface of said tube for supporting said modules therein.

8. The assembly of claim 7 in which said sleeve means comprises a rigidly generally-cylindrical sleeve extending about and secured to each of said rod lenses, said ribs being disposed between said intermediate and end portions and extending radially outwardly therefrom.

9. The assembly of claim 8 in which said ribs of each sleeve are spaced uniformly from the longitudinal mid point of said sleeve and are spaced apart a distance of approximately $$c = 2\sqrt{h^2 + \frac{L^2}{8} - 2hD}$$

where c is the distance between said ribs, h is the radial height of each rib, L is the total sleeve length, and D is the inside diameter of said tube.

10. The assembly of claim 8 in which said ribs of each sleeve are spaced uniformly from the longitudinal mid point of said sleeve and are spaced apart a distance of approximately $$c = \frac{L}{\sqrt{2}}$$

where c is the distance between the ribs and L is the total length of the sleeve.

11. The assembly of claim 8 in which said ribs are formed integrally with said intermediate and end portions.

12. The assembly of claim 7 in which the rod lens of at least one of said modules comprises a plurality of lens elements disposed in axial alignment.

13. The assembly of claim 7 in which each of said tubular end portions terminates in an annular contact surface extending in a plane normal to the axis of the module thereof, said contact surfaces of successive modules of said series being in mutual engagement.

14. The assembly of claim 13 in which means are provided for urging said contact surfaces of successive modules of said series into mutual engagement.

15. The assembly of claim 13 in which said tubular end portions of successive lens modules are connected by bands of stretchable and elastic plastic film wrapped thereabout.

16. A modular rod lens assembly comprising a straight semi-rigid tube capable of limited flexure, and a series of lens modules disposed in end-to-end relation therein, each module comprising a rigid and generally cylindrical sleeve having an intermediate portion and a pair of end portions and an elongated rod lens having a pair of oppositely-directed end faces and being disposed entirely within said intermediate portion of said sleeve, said end portions projecting endwise beyond said oppositely-directed end faces, said intermediate and end portions of said sleeve of each module having outside dimensions substantially smaller than the interior of said tube to define an annular space therebetween, and a pair of narrow ribs extending outwardly from each sleeve between said intermediate and end portions thereof for engaging the inside of said tube, whereby, said ribs maintain said modules in aligned relation within said tube when the same is in straight condition and provide bearing surfaces for supporting said modules within said tube when the same is flexed.

17. The assembly of claim 16 in which said end portions terminate in annular contact surfaces extending in planes normal to the longitudinal axis of said sleeve.

18. The assembly of claim 17 in which spring means are provided for urging said modules axially to maintain the contact surfaces of successive modules in engagement with each other.

19. The assembly of claim 16 in which said ribs are formed integrally with said intermediate and end portions of each sleeve.

20. The assembly of claim 16 in which said rod lens of at least one of said modules comprises a plurality of lens elements arranged in axial alignment.

21. The assembly of claim 16 in which said ribs of each sleeve are spaced uniformly from the longitudinal mid point of said sleeve and are spaced apart a distance of approximately $$c = 2\sqrt{h^2 + \frac{L^2}{8} - 2hD}$$

where c is the distance between said ribs, h is the radial height of each rib, L is the total sleeve length, and D is the inside diameter of said tube.

22. The assembly of claim 16 in which said ribs of each sleeve are spaced uniformly from the longitudinal mid point of said sleeve and are spaced apart a distance of approximately $$c = \frac{L}{\sqrt{2}}$$

where c is the distance between the ribs and L is the total length of the sleeve.

23. The assembly of claim 16 in which said tubular end portions of successive lens modules are connected by bands of stretchable and elastic plastic film extending thereabout.

24. A method of forming a modular rod lens assembly comprising the steps of introducing a cylindrical rod lens into one end of an open-ended sleeve having a length substantially greater than the length of said lens until said lens engages a stop element temporarily inserted and precisely positioned in the sleeve's opposite end, and thereafter securing said lens within said sleeve and withdrawing said stop element, said sleeve being provided with a pair of outwardly-projecting annular ribs spaced from the ends of said sleeve, said ribs providing smooth bearing surfaces for slidably engaging the inner surface of an elongated flexible barrel, said method including the additional steps of cleaning said lens module and thereafter slidably shifting the same into position within the bore of a rod lens barrel.

25. The method of claim 24 in which said introducing, securing, withdrawing, and cleaning steps are repeated to produce a plurality of rod lens modules, said plurality of rod lens modules being successively inserted into the bore of said barrel to produce a rod lens system having the modules thereof in end-to-end engagement.

* * * * *